United States Patent [19]
Murakami et al.

[11] 3,951,962
[45] Apr. 20, 1976

[54] NOVEL N-ALKENYLTETRACYCLINE DERIVATIVES

[75] Inventors: Masuo Murakami, Tokyo; Masaru Iwanami, Yokohama; Tadao Shibanuma, Asaka; Masaharu Fujimoto, Tokyo; Norio Sato; Ryutaro Kawai, both of Shiraoka; Kuniichiro Yano, Tokorozawa, all of Japan

[73] Assignee: Yamanouchi Pharmaceutical Co., Ltd., Tokyo, Japan

[22] Filed: Mar. 19, 1975

[21] Appl. No.: 560,110

Related U.S. Application Data

[60] Continuation-in-part of Ser. No. 415,529, Nov. 14, 1973, abandoned, which is a division of Ser. No. 205,414, Dec. 6, 1971, Pat. No. 3,818,274.

[52] U.S. Cl. ............... 260/240 R; 260/347.3; 260/559 AT
[51] Int. Cl.² ............... C07D 307/02; C07C 103/19
[58] Field of Search ....... 260/559 AT, 240 R, 347.3

[56] References Cited
UNITED STATES PATENTS

| | | | |
|---|---|---|---|
| 3,028,409 | 4/1962 | Stephens | 260/456 |
| 3,808,274 | 4/1974 | Murakami et al. | 260/559 AT |

Primary Examiner—John D. Randolph
Attorney, Agent, or Firm—Burgess Ryan and Wayne

[57] ABSTRACT

N-alkenyltetracycline derivatives, for example, N-[1-methyl-2(2-thienyl)-1-butenyl]tetracycline represented by the formula

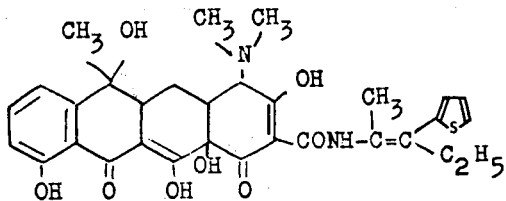

The compounds have excellent antibacterial action as compared with tetracycline.

7 Claims, No Drawings

NOVEL N-ALKENYLTETRACYCLINE DERIVATIVES

This application is a continuation-in-part of Ser. No. 415,529, filed Nov. 14, 1973, now abandoned, which was a divisional of U.S. application Ser. No. 205,414 filed Dec. 6, 1971 and now U.S. Pat. No. 3,818,274 granted Apr. 30, 1974.

The present invention relates to N-alkenyltetracycline derivatives having excellent antibacterial action. More particularly, the invention relates to N-alkyenyltetracycline derivatives represented by the formula III

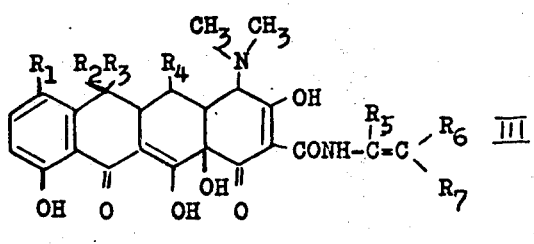

wherein $R_1$ represents a hydrogen atom, a halogen atom, or a dimethylamino group; $R_2$ represents a hydrogen atom or a methyl group; $R_3$ represents a hydrogen atom or a hydroxyl group; said $R_2$ and $R_3$ when combined with each other form a methylene group, $R_4$ represents a hydrogen atom or a hydroxyl group; and $R_5$, $R_6$ and $R_7$, which may be the same or different, each represent a hydrogen atom, a halogen atom, a nitro group, a cyano group, a hydroxyl group, a mercapto group, a carboxyl group, a carbamoyl group, an alkoxyl group such as methoxy and ethoxy, an aryloxy group such as phenoxy, an alkylthio group such as ethylthio, an arylthio group such as phenylthio, an alkoxycarbonyl group such as ethoxycarbonyl and t-butoxycarbonyl, an aryloxycarbonyl group such as phenoxycarbonyl, an alkylsulfonyl group such as methylsulfonyl and allylsulfonyl, an arylsulfonyl group such as phenylsulfonyl, an alkanoyl group such as acetyl and t-butyryl, an aroyl group such as benzoyl, an alkylcarbamoyl group such as ethylcarbamoyl, an arylcarbamoyl group such as phenylcarbamoyl, an alkyl group such as a saturated alkyl group, e.g., methyl, ethyl, propyl, isopropyl, isobutyl, t-butyl, amyl, and octyl and an unsaturated alkyl group, e.g., 2-propionyl and allyl, a cycloalkyl group such as a saturated cycloalkyl group, e.g., cyclohexyl, cycloheptyl, etc., and an unsaturated cycloalkyl group, e.g., cyclohexenyl and indenyl, an aryl group such as phenyl and naphthyl, an aralkyl group such as benzyl, phenethyl, and 2-phenylisobutyl, and a heterocyclic ring group such as pyridyl, pyrimidyl, thienyl, pyranyl, pyrazolyl, furyl, thiazolyl, and chromanyl.

Two members of the groups $R_5$, $R_6$ and $R_7$ may combine to form an alkylene group such as a saturated alkylene group, e.g., trimethylene, tetramethylene, pentamethylene, etc.; an unsaturated alkylene group, e.g., butenylene, etc.; a heteroatom-containing saturated alkylene group, e.g., 2-azatetramethylene (—CH$_2$—NH—CH$_2$—CH$_2$—), 2-thiatrimethylene (—CH$_2$—S—CH$_2$—), 2-oxatetramethylene (—CH$_2$—O—CH$_2$—), 1-aza-3-oxatetramethylene (—NH—CH$_2$—O—CH$_2$—), etc., and a heteroatom-containing unsaturated alkylene group, e.g., 1-oxa-2-butenylene (—O—CH=CH—CH$_2$—), etc. Furthermore, each of the CH—$R_5$, $R_6$ and $R_7$ may have, as a substituent, a halogen atom, a nitro group, a cyano group, an amino group, a dimethylamino group, an imino group, a hydroxyl group, a mercapto group, a formyl group, a carboxyl group, a sulfone group, a methoxy group, a butoxyl group, a methylthio group, a phenoxy group, a phenylthio group, a methoxycarbonyl group, an ethoxycarbonyl group, a phenoxycarbonyl group, a methylsulfonyl group, a phenylsulfonyl group, a p-toluenesulfonyl group, an acetyl group, a benzoyl group, a furyl group, or a thienyl group and further other groups except alkyl, cycloalkyl, and alkylene shown by the groups $R_5$, $R_6$ and $R_7$ may have the above substituent or a methyl group, an ethyl group, a butyl group, an isobutyl group, a t-butyl group, an allyl group, a cyclohexyl group, a tetramethylene group, a butadienylene (—CH=CH—CH=CH—), a 3-ethylbutadienylene

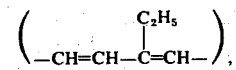

etc.

The compounds of this invention represented by the formula III are compounds that have never been reported in any references and are valuable antibiotics having excellent antibacterial power which are effective not only against grampositive and gramnegative bacteria but also against tetracycline resisting bacteria.

The compounds of this invention represented by the formula III are prepared by the reaction of the tetracycline represented by the formula I

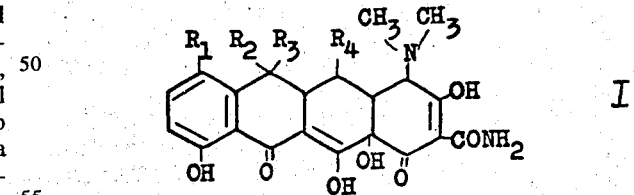

wherein $R_1$, $R_2$, $R_3$ and $R_4$ have the same significance as in the formula III with the enamine compound represented by the formula II

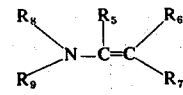

wherein $R_5$, $R_6$ and $R_7$ have the same significance as in the formula III and $R_8$ and $R_9$, which may be same or different, each represents an alkyl group such as methyl, ethyl, propyl, isobutyl and t-butyl or an aryl group such as phenyl, said $R_8$ and $R_9$ may combine with a nitrogen atom to form a heterocyclic ring, which may contain a heteroatom, such as a piperidine ring, a pyrrolidine ring, a morpholine ring, or a quinoline ring.

It is not known that the enamine compound having an acid amide structure as the compound of the formula III is obtained by the reaction of the compound having a carbamoyl structure as the compound of the formula I with the enamine type compound as the compound of formula II, that is, such a reaction is a novel reaction discovered first by the inventors.

Examples of the tetracyclines represented by the above formula I, which is used as a starting material in the aforesaid reaction includes, e.g., tetracycline, 5-oxytetracycline, 7-chlorotetracycline, 7-bromotetracycline, 5-oxy-7-chlorotetracycline, 6-deoxy-5-oxytetracycline, 6-deoxytetracycline, 6-deoxy-6-demethyltetracycline, 6-demethyltetracycline, 6-demethyl-7-chlorotetracycline, 6-methylenetetracycline, 6-methylene-5-oxytetracycline, 5-oxy-6-demethyltetracycline, and 7-dimethylamino-6-demethyl-6-deoxytetracycline.

Among the enamine compounds shown by the formula II, there may be included novel compounds and they may be prepared by the reaction of corresponding ketones and amines (see; "ENAMINES" written by A. Gilbert Cook, published by Marcel Dekker Co. in 1969).

The reaction of preparing the compounds of this invention is conducted by reacting the tetracycline of the formula I and an equimolar to excessive molar amount, preferably about twice by mol that of the enamine compound of the formula II in an organic solvent such as dimethyl formamide, and the like. The reaction is conducted at room temperature or under cooling or heating but is ordinarily conducted at room temperature in the presence of a mineral acid such as hydrochloric acid, hydrobromic acid, etc., with stirring for few hours. In this case, however, a mineral acid salt of the tetracycline I and/or a mineral acid (immonium salt) of the enamine compound II may be used in place of the mineral acid.

The desired compounds III of this invention thus prepared may be isolated from the reaction product liquid by an ordinary chemical operation such as extraction, etc., and if necessary, the product may be further purified by reprecipitation, recrystallization and the like.

In the following experiments, the antibacterial actions of the compounds of this invention to a standard strain and a tetracycline resisting bacterium were compared with those of tetracycline.

Experiment I

To an ordinary agar culture medium (pH 7) containing 25, 6.25, 1.56, 0.39 or 0.9 mcg/ml of the test sample was inoculated
(A) a standard strain, Staphylococcus aureus FDA 209p or (B) a tetracycline resisting bacteria, Staphylococcus aureus Ōnuma by an agar dilution method and when the bacterium was cultivated for 24 hours at 37°C, it was observed whether the bacterium grew or not. The case where the growth of the bacterium was observed was denoted by (+) and the case where the growth was not observed was denoted by (−), the results being shown in Table I.

Table 1

| Compounds | Organisms | Concentration of Sample (mcg/ml) | | | | |
|---|---|---|---|---|---|---|
| | | 25 | 6.25 | 1.56 | 0.39 | 0.09 |
| Tetracycline | A | − | − | − | − | + |
| | B | + | + | + | + | + |
| Product of Example 2 | A | − | − | − | + | + |
| | B | − | − | − | + | + |
| 6 | A | − | − | − | + | + |
| | B | − | − | − | + | + |
| 14 | A | − | − | − | + | + |
| | B | − | − | − | + | + |
| 16 | A | − | − | − | − | + |
| | B | − | − | − | − | + |
| 17 | A | − | − | − | + | + |
| | B | − | − | − | + | + |
| 18 | A | − | − | − | + | + |
| | B | − | − | − | + | + |
| 20 | A | − | − | − | + | + |
| | B | − | − | − | + | + |
| 27 | A | − | − | − | − | + |
| | B | − | − | − | + | + |
| 28 | A | − | − | − | − | + |
| | B | − | − | − | − | + |
| 29 | A | − | − | − | + | + |
| | B | − | − | − | + | + |
| 36 | A | − | − | − | + | + |
| | B | − | − | − | + | + |
| 38 | A | − | − | − | + | + |
| | B | − | − | − | + | + |
| 42 | A | − | − | − | + | + |
| | B | − | − | − | + | + |
| 43 | A | − | − | − | + | + |
| | B | − | − | − | + | + |
| 44 | A | − | − | − | + | + |
| | B | − | − | − | + | + |
| 45 | A | − | − | − | + | + |
| | B | − | − | − | + | + |
| 50 | A | − | − | − | − | + |
| | B | − | − | − | + | + |
| 53 | A | − | − | − | − | + |
| | B | − | − | − | − | + |
| 56 | A | − | − | − | + | + |
| | B | − | − | − | + | + |
| 68 | A | − | − | − | + | + |
| | B | − | − | − | + | + |
| 69 | A | − | − | − | + | + |
| | B | − | − | − | + | + |
| 70 | A | − | − | − | + | + |
| | B | − | − | − | + | + |
| 73 | A | − | − | − | + | + |
| | B | − | − | − | + | + |
| 75 | A | − | − | − | − | + |
| | B | − | − | − | + | + |
| 78 | A | − | − | − | − | + |
| | B | − | − | − | − | − |
| 83 | A | − | − | − | − | + |
| | B | − | − | − | − | + |
| 85 | A | − | − | − | + | + |
| | B | − | − | − | + | + |
| 86 | A | − | − | − | + | + |
| | B | − | − | − | + | + |
| 87 | A | − | − | − | + | + |
| | B | − | − | − | + | + |
| 88 | A | − | − | − | + | + |
| | B | − | − | − | + | + |
| 89 | A | − | − | − | − | + |
| | B | − | − | − | + | + |
| 90 | A | − | − | − | − | + |
| | B | − | − | − | − | + |
| 91 | A | − | − | − | − | + |
| | B | − | − | − | + | + |
| 93 | A | − | − | − | + | + |
| | B | − | − | − | + | + |
| 94 | A | − | − | − | + | + |
| | B | − | − | − | + | + |
| 98 | A | − | − | − | − | + |
| | B | − | − | − | − | + |
| 104 | A | − | − | − | + | + |
| | B | − | − | − | + | + |
| 105 | A | − | − | − | + | + |
| | B | − | − | − | + | + |
| 108 | A | − | − | − | + | + |
| | B | − | − | − | + | + |
| 109 | A | − | − | − | + | + |
| | B | − | − | − | + | + |

Table 1-continued

| Compounds | Organisms | Concentration of Sample (mcg/ml) | | | | |
|---|---|---|---|---|---|---|
| | | 25 | 6.25 | 1.56 | 0.39 | 0.09 |
| 113 | B | − | − | − | + | + |
| | A | − | − | − | − | + |
| 116 | B | − | − | − | + | + |
| | A | − | − | − | + | + |
| 119 | B | − | − | − | + | + |
| | A | − | − | − | + | + |
| 121 | B | − | − | − | + | + |
| | A | − | − | − | − | − |
| 127 | B | − | − | − | − | − |
| | A | − | − | − | − | + |
| 128 | B | − | − | − | − | + |
| | A | − | − | − | − | + |
| 129 | B | − | − | − | + | + |
| | A | − | − | − | + | + |
| 130 | B | − | − | − | + | + |
| | A | − | − | − | + | + |
| 131 | B | − | − | − | + | + |
| | A | − | − | − | − | + |
| 132 | B | − | − | − | − | + |
| | A | − | − | − | − | + |
| 133 | B | − | − | − | − | + |
| | A | − | − | − | − | − |
| 135 | B | − | − | − | + | + |
| | A | − | − | − | − | − |
| 136 | B | − | − | − | − | − |
| | A | − | − | − | − | + |
| 137 | B | − | − | − | − | + |
| | A | − | − | − | + | + |
| 138 | B | − | − | − | + | + |
| | A | − | − | − | − | + |
| 139 | B | − | − | − | − | + |
| | A | − | − | − | − | − |
| 141 | B | − | − | − | − | + |
| | A | − | − | − | − | + |
| 142 | B | − | − | − | − | + |
| | A | − | − | − | + | + |
| 143 | B | − | − | − | + | + |
| | A | − | − | − | − | + |
| 144 | B | − | − | − | + | + |

As is clear from Table I, the compounds of this invention have excellent antibacterial activity with respect to the tetracycline resisting bacterium.

In the following experiment, the antibacterial spectra of the compounds of this invention were compared with those of tetracycline.

Experiment II

To a heart infusion agar culture medium containing 100, 50, 25, 12.5, 6.25, 3.13 or 1.56 mcg/ml of the test sample was inoculated (A) Staphylococcus aureus FDA 209p, (B) Staphylococcus aureus Onuma, (C) Staphylococcus aureus Shimanishi, (D) E. coli, (E) Proteus vulgaris, (F) Pseudomonas aeroginosa, (G) Salmonella typhi H901W, or (H) Shigella sonnei II 37148 and then the bacerium was cultivated for 24 hours at 37°C. It was observed whether the bacterium grew or not. The case where the growth of the bacterium was observed was denoted by (+) and the case where the growth was not observed was denoted by (−), the results being shown in Table II.

| Compounds | Organisms | Concentration of Sample (mcg/ml) | | | | | | |
|---|---|---|---|---|---|---|---|---|
| | | 100 | 50 | 25 | 12.5 | 6.25 | 3.13 | 1.56 |
| Tetracycline | A | − | − | − | − | − | − | + |
| | B | + | + | + | + | + | + | + |
| | C | + | + | + | + | + | + | + |
| | D | − | − | − | − | − | − | − |
| | E | − | − | − | − | − | + | + |
| | F | − | + | + | + | + | + | + |
| | G | − | − | − | − | − | + | + |
| | H | − | − | − | − | − | − | + |
| | A | − | − | − | − | − | − | − |
| | B | − | − | − | − | − | − | − |
| | C | − | − | − | − | − | − | + |
| | D | − | − | − | − | − | − | + |

| Compounds | Organisms | Concentration of Sample (mcg/ml) | | | | | | |
|---|---|---|---|---|---|---|---|---|
| | | 100 | 50 | 25 | 12.5 | 6.25 | 3.13 | 1.56 |
| Product of Example 17 | E | − | − | − | + | + | + | + |
| | F | + | + | + | + | + | + | + |
| | G | − | − | − | − | − | + | + |
| | H | − | − | − | − | − | + | + |
| | A | − | − | − | − | − | − | − |
| | B | − | − | − | − | − | + | + |
| | C | − | − | − | − | − | + | + |
| | D | − | − | − | + | + | + | + |
| Product of Example 123 | E | − | − | − | − | + | + | + |
| | F | + | + | + | + | + | + | + |
| | G | − | − | − | − | + | + | + |
| | H | − | − | − | − | − | + | + |

As is clear from the above results shown in the Table II, the compounds of this invention had broad antibacterial spectra.

The invention will now be illustrated in and by the following examples.

EXAMPLE 1

In 7 ml of dimethylformamide was dissolved 1.0g of tetracycline hydrochloride and after adding to the solution 0.7g of a mixture of 3-methyl-2-piperidino-2-butene and 3-methyl-2-piperidino-1-butene, the mixture was stirred for 4 hours at room temperature. After the reaction was over, the solvent was distilled away from the reaction product liquid and water was added to the residue to form a precipitate, which was recovered by filtration. The precipitate thus recovered was dissolved in 20 ml of chloroform, the solution was washed with water, 2% aqueous acetic acid solution, and then water, and after drying the solution over anhydrous sodium sulfate, chloroform was distilled away.

Petroleum ether was added to the residue and the crystalline powder of N-(1,2-dimethyl-1-propenyl)tetracycline thus precipitated was recovered by filtration. The amount of the product was 0.5g.

| Elemental analysis as $C_{27}H_{32}N_2O_8$: | | |
|---|---|---|
| | C (%) | H (%) | N (%) |
| Calculated: | 63.27 | 6.29 | 5.47 |
| Found: | 63.36 | 6.29 | 5.46 |

EXAMPLE 2

In 10 ml of dimethylformamide was dissolved 1.0g of tetracycline hydrochloride and after adding to the solution 0.895g of 1-phenyl-2-piperidino-1-butene, the mixture was stirred for 4 hours at room temperature. After the reaction was over, the solvent was distilled away from the reaction product liquid and after adding water to the residue, the product was extracted with chloroform.

The chloroform was distilled away, ether and petroleum ether were added to the residue, and the precipitate thus formed was recovered by filtration. The precipitate was dissolved in chloroform, the solution was then washed with a 2% aqueous acetic acid solution and then with water, and chloroform was distilled away. When an ether-petroleum ether solvent was added to the residue followed by purification, about 1.0g of N-(1-ethyl-2-phenylethenyl)tetracycline was obtained. However, the product contained a small amount of a hydrogen rearrangement product, N-(1-benzyl-1-propenyl)tetracycline.

| Elemental analysis as $C_{32}H_{34}N_2O_8$: | | | |
|---|---|---|---|
| | C (%) | H (%) | N (%) |
| Calculated: | 66.89 | 5.96 | 4.87 |
| Found: | 66.53 | 5.92 | 4.89 |

EXAMPLE 3

In 5.5 ml of dimethylformamide was dissolved 0.8g of tetracycline hydrochloride and after adding to the solution 0.7g of 1-(4-methylthiazole-2-yl)-2-piperidinopropene, the mixture was heated to 70°C for 3 hours. After the reaction was over, the solvent was distilled away under a reduced pressure and after adding to the residue 5 ml of water, the product was extracted with chloroform. After washing the extract with 2% aqueous acetic acid solution and then 2% aqueous sodium bicarbonate solution, the solution was distilled away and then 10 ml of ether was added to the residue to form a precipitate, which was recovered by filtration to provide 0.8g of a yellow powder of N-[1-methyl-2-(4-methylthiazole-2-yl)ethenyl]tetracycline having a melting point of 150° – 157°C (decomposed).

| Elemental analysis as $C_{29}H_{31}N_3O_8S.H_2O$: | | | | |
|---|---|---|---|---|
| | C (%) | H (%) | N (%) | S (%) |
| Calculated: | 58.09 | 5.55 | 7.01 | 5.35 |
| Found: | 57.74 | 5.28 | 6.75 | 5.24 |

EXAMPLE 4

In 5 ml of dimethylformamide was dissolved 0.7g of tetracycline hydrochloride and after adding to the solution 0.7g of 1-(2,4-dimethylpyrimidine-6-yl)-2-piperidinopropene, the mixture was heated to 70°C for 4 hours. After the reaction was over, the solvent was distilled away from the reaction product liquid under a reduced pressure and after adding to the residue 5 ml of water, the product was extracted by chloroform. After washing the extract with 2% aqueous acetic acid solution and then 2% aqueous sodium bicarbonate solution, the solvent was distilled away and then 10 ml of ether was added to the residue to form a precipitate, which was recovered by filtration to provide 0.3g of N-[1-methyl-2-(2,4-dimethylpyrimidine-6-yl)ethenyl]tetracycline having a melting point of 154°–162°C (decomposed).

| Elemental analysis as $C_{31}H_{34}N_4O_8.H_2O$: | | | |
|---|---|---|---|
| | C (%) | H (%) | N (%) |
| Calculated: | 61.17 | 5.97 | 9.21 |
| Found: | 61.08 | 5.70 | 9.13 |

EXAMPLE 5

In 14 ml of dimethylformamide was dissolved 2.0g of tetracycline hydrochloride and after adding further to the solution 2.1g of 2-morpholino-2-undecene, the mixture was stirred for 15 hours at room temperature. After the reaction was over, the solvent was distilled away from the reaction product liquid and after adding water to the residue, the product was extracted with chloroform. The extract was washed with water, 2% aqueous acetic acid solution, 2% aqueous sodium bicarbonate solution, and then water, and after drying over anhydrous magnesium sulfate, the solvent was distilled away under a reduced pressure and ether and petroleum ether were added to the residue, thereafter the precipitate thus formed was recovered by filtration to provide 0.5g of N-(1-methyl-1-decenyl)tetracycline.

| Elemental analysis as $C_{33}H_{44}N_2O_8$: | | | |
|---|---|---|---|
| | C (%) | H (%) | N (%) |
| Calculated: | 66.42 | 7.48 | 4.70 |
| Found: | 66.51 | 7.25 | 4.58 |

EXAMPLE 6

In 7 ml of dimethylformamide was dissolved 1.0g of tetracycline hydrochloride and after adding to the solution 1.1g of 1-p-nitrophenyl-2-morpholino-1-propene, the mixture was stirred for 14 hours at room temperature. After the reaction was over, the solvent was distilled away under a reduced pressure and after adding water to the residue, the product was extracted with chloroform. The extract was washed with water, 2% aqueous acetic acid solution, 2% aqueous sodium bicarbonate solution, and then water and after drying over anhydrous magnesium sulfate, the solvent was distilled away under a reduced pressure. Ether and petroleum ether were added to the residue and the precipitate thus formed was recovered by filtration to provide 0.8g of N-[2-(p-nitrophenyl)-1-methylethenyl]tetracycline.

| Elemental analysis as $C_{31}H_{31}N_3O_{10}$: | | | |
|---|---|---|---|
| | C (%) | H (%) | N (%) |
| Calculated: | 61.48 | 5.16 | 6.94 |
| Found: | 61.23 | 5.28 | 6.72 |

EXAMPLE 7

In 10 ml of dimethylformamide was dissolved 1.0g of tetracycline hydrochloride and after adding 0.7g of N-cyclopentenyl-piperidine to the solution, the mixture was stirred for 5 hours at room temperature. After the reaction was over, the solvent was distilled away from the reaction product liquid under a reduced pressure and water was added to the residue, whereby a precipitate was formed. The precipitate was recovered by filtration and washed with water to provide 0.3g of N-cyclopentenyltetracycline piperidine salt.

Nuclear magnetic resonance: alkene hydrogen 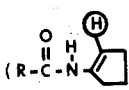

τ 4.2 (1 H) (CDCl₃)

Elemental analysis as $C_{32}H_{41}N_3O_8 \cdot H_2O$:

|  | C (%) | H (%) | N (%) |
|---|---|---|---|
| Calculated: | 62.62 | 7.06 | 6.85 |
| Found: | 62.50 | 6.77 | 6.56 |

EXAMPLE 8

In 10 ml of dimethylformamide was dissolved 1.0g of tetracycline hydrochloride and after adding to the solution 0.7g of N-cyclohexenylpyrrolidine, the mixture was stirred for 5 hours at room temperature. After the reaction was over, the solvent was distilled away from the reaction product liquid under a reduced pressure and when water was added to the residue thus obtained and the pH of the solution was adjusted to 5 with 1 N hydrochloric acid, a precipitate was formed. The precipitate recovered by filtration was washed with water, and dissolved in chloroform, and reprecipitated from chloroform-ether to provide 0.3g of N-cyclohexenyltetracycline.

EXAMPLE 9

In 10 ml of dimethylformamide was dissolved 1.0g of tetracycline hydrochloride and after adding 0.7g of N-4-methylcyclohexenylpiperidine to the solution, the mixture was stirred for 5 hours at room temperature. After the reaction was over, the solvent was distilled away from the reaction product liquid under a reduced pressure and when water was added to the residue thus obtained, a precipitate was formed. The precipitate was recovered by filtration and washed with water to provide 0.7g of N-4-methylcyclohexenyltetracycline piperidine salt.

EXAMPLE 10

In 14 ml of dimethylformamide was dissolved 1.45g of chlorotetracycline hydrochloride and after adding dropwise to the solution 0.93g of 1-piperidinocyclohexene, the mixture was stirred for 5 hours at room temperature. After the reaction was over, the solvent was distilled away from the reaction product liquid under a reduced pressure and when water was added to the residue thus obtained, a solid product was precipitated. The precipitate was recovered by filtration, and after drying reprecipitated from chloroform-ether to provide 0.4g of N-cyclohexenylchlorotetracycline.

Nuclear magnetic resonance: Alkene hydrogen 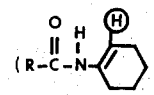

τ 3.88 (1H) (CDCl₃)

Elemental analysis as $C_{28}H_{31}N_2O_2Cl$:

|  | C (%) | H (%) | N (%) | Cl (%) |
|---|---|---|---|---|
| Calculated: | 60.16 | 5.59 | 5.01 | 6.34 |
| Found: | 59.71 | 6.01 | 5.40 | 6.00 |

EXAMPLE 11

In 2.5 ml of dimethylformamide was dissolved 213 mg of 6-methylenetetracycline hydrochloride and after adding to the solution 165 mg of N-cyclohexenyl piperidine, the mixture was stirred for 3 hours at room temperature. After the reaction was over, piperidine hydrochloride thus precipitated was filtered off and 7 ml of methanol was added to the filtrate, whereby crystalline N-cyclohexenyl6-methylenetetracycline was precipitated. The amount of the product was 183 mg. The product was recovered by filtration and purified by recrystallizing from dimethylformamide-methanol.

Nuclear magnetic resonance: alkene hydrogen 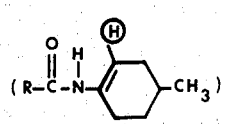

τ 3.9 (1H) (CDCl₃)

Elemental analysis as $C_{34}H_{45}N_3O_8 \cdot H_2O$:

|  | C (%) | H (%) | N (%) |
|---|---|---|---|
| Calculated: | 63.63 | 7.38 | 6.55 |
| Found: | 63.90 | 7.21 | 6.30 |

Nuclear magnetic resonance: Alkene hydrogen 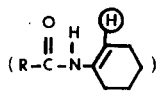

τ 4.0 (1H) (CD Cl₃)

Elemental analysis as $C_{28}H_{30}N_2O_7$:

|  | C (%) | H (%) | N (%) |
|---|---|---|---|
| Calculated: | 66.39 | 5.97 | 5.53 |
| Found: | 65.97 | 6.21 | 5.75 |

EXAMPLE 12

In 10 ml of dimethylformamide was dissolved 1.0g of tetracycline and after adding to the solution 0.74g of N-cyclohexylidene piperidinium perchlorate, the mixture was stirred for 4 hours at room temperature. Then, 0.192g of piperidine was added to the solution and mixture was further stirred for 4 hours. After the reaction was over, the solvent was distilled away from the reaction product liquid under a reduced pressure and after adding 15 ml of water to the residue obtained, the product was extracted twice each with 15 ml of chloroform. After washing the extract with water, the extract was concentrated and mixed with ether and petroleum ether, whereby a precipitate was formed. The precipitate was dissolved in chloroform and after washing the solution with 2% aqueous acetic acid solution and water, ether and then petroleum ether were added to the solution, whereby a precipitate was formed. The precipitate was recovered by filtration and dissolved in a small amount of chloroform and after adding ether and petroleum ether to the solution, the product was reprecipitated to provide 0.1g of N-cyclohexenyltetracycline.

Nuclear magnetic resonance: Alkene hydrogen 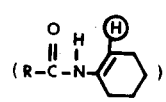

τ 4.0 (1H) (CD Cl₃)

Elemental analysis as $C_{28}H_{32}N_2O_8$:

|  | C (%) | H (%) | N (%) |
|---|---|---|---|
| Calculated: | 64.11 | 6.15 | 5.34 |
| Found: | 53.99 | 6.04 | 5.27 |

EXAMPLE 13

In 7 ml of dimethylformamide was dissolved 1.0g of tetracycline hydrochloride and after adding to the solution 1.0g of N-cyclohexenylmorpholine, the mixture was stirred for 14 hours at room temperature. After the reaction was over, the solvent was distilled away under a reduced pressure, water was added to the residue obtained, and the solid precipitated was extracted with chloroform. The extract was washed with water, 2% aqueous acetic acid solution, 2% aqueous sodium bicarbonate solution, and then water and then after drying the extract over anhydrous magnesium sulfate, the solvent was distilled away under a reduced pressure. Then, ether and petroleum ether was added to the residue and the crystalline powder thus precipitated was recovered by filtration to provide 0.5g of N-cyclohexenyltetracycline.

Nuclear magnetic resonance: Alkene hydrogen 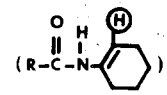

τ 4.0 (1H) (CD Cl₃)

EXAMPLE 14

In 10 ml of dimethylformamide was dissolved 1.0g of tetracycline hydrochloride and after adding 1.0g of N-(2-phenylcyclohexenyl)piperidine to the solution, the mixture was stirred for 5 hours at room temperature. After the reaction was over, the solvent was distilled away from the reaction product liquid under a reduced pressure and the residue was mixed with chloroform. The mixture was stirred and after filtering off insoluble matters, the remaining solution was washed with 3% aqueous acetic acid solution and then water and after drying the solution over anhydrous magnesium sulfate, the solvent was distilled away under a reduced pressure. Then, ether-petroleum ether (1 : 5 in volume ratio) was added to the residue and the crystalline solid thus precipitated was recovered by filtration to provide 120 mg of N-(2-phenylcyclohexenyl)-tetracycline.

Elemental analysis as $C_{34}H_{36}O_xN_2.H_2O$:

|  | C (%) | H (%) | N (%) |
|---|---|---|---|
| Calculated: | 66.01 | 6.19 | 4.53 |
| Found: | 65.85 | 6.24 | 4.43 |

EXAMPLE 15

In 48 ml of dimethylformamide was dissolved 4.88g of tetracycline hydrochloride and after adding to the solution 4.35g of N-(3,4-dihydro-2-naphthyl)piperidine, the mixture was stirred for 16 hours at 60°C. After the reaction was over, the reaction product liquid was concentrated under a reduced pressure and the residue dissolved in chloroform followed by washing four times with water. When the chloroform layer thus formed was concentrated under a reduced pressure and mixed with ether, a precipitate was formed. The precipitate was recovered by filtration, dissolved in chloroform, and the solution was washed twice with 2% aqueous acetic acid solution and dried over anhydrous magnesium sulfate. Then, the solution was concentrated under a reduced pressure, ether was added to the concentrate, and the precipitate thus formed was recovered by filtration to provide 2.2g of N-(3,4-dihydro-2-naphthyl)tetracycline.

Elemental analysis as $C_{32}H_{32}N_2O_8$:

|  | C (%) | H (%) | N (%) |
|---|---|---|---|
| Calculated: | 67.12 | 5.63 | 4.89 |
| Found: | 66.90 | 5.91 | 5.00 |

EXAMPLE 16

In 18 ml of dimethylformamide was dissolved 2g of tetracycline hydrochloride and after adding 1.91g of 2-piperidino-3-p-tolyl-2-butene, the mixture was stirred for about 6 hours at room temperature. After the reaction was over, the solvent was distilled away from the reaction product liquid under a reduced pressure and when ether and petroleum ether were added to the residue, a precipitate was formed. The precipitate was recovered by filtration, dissolved in chloroform, after washing the solution with 2% aqueous acetic acid solution and then water, the solution was concentrated, and then ether and petroleum ether were added to the solution, whereby a precipitate was formed. The precipitate was recovered by filtration, dissolved in chloroform, and after adding ether and petroleum ether to the solution, the product was reprecipitated to provide 2g of N-(1-methyl-2-p-tolyl-1-propenyl)tetracycline.

Elemental analysis as $C_{33}H_{36}N_2O_8$:

|  | C (%) | H (%) | N (%) |
|---|---|---|---|
| Calculated: | 67.33 | 6.16 | 4.76 |
| Found: | 67.22 | 6.43 | 4.95 |

EXAMPLE 17

In 18 ml of dimethylformamide was dissolved 2g of tetracycline hydrochloride and after adding to the solution 2.03g of 3-methyl-3-p-tolyl-2-piperidino-1-butene, the mixture was stirred for about 6 hours at room temperature. Thereafter, by following the same procedure as in Example 16, 2g of N-[1-(1-methyl-1-p-tolylethyl)ethenyl]-tetracycline was obtained.

Elemental analysis as $C_{34}H_{38}N_2O_8$:

|  | C (%) | H (%) | N (%) |
|---|---|---|---|
| Calculated: | 67.76 | 6.36 | 4.65 |
| Found: | 67.69 | 6.33 | 4.80 |

EXAMPLE 18

In 18 ml of dimethylformamide was dissolved 2g of tetracycline hydrochloride and after adding to the solution 1.8g of 1-(2-furyl)-2-morpholino-1-propene, the mixture was stirred for about 6 hours at room temperature. Thereafter, by following the same procedure as in Example 16, 0.2g of N-[1-methyl-2-(2-furyl)-ethenyl] tetracycline was obtained.

Elemental analysis as $C_{29}H_{30}N_2O_9$:

|  | C (%) | H (%) | N (%) |
|---|---|---|---|
| Calculated: | 63.27 | 5.49 | 5.09 |
| Found: | 63.55 | 5.75 | 4.91 |

EXAMPLE 19

In 7 ml of dimethylformamide were dissolved 1g of tetracycline hydrochloride and 1g of N-(6-ethyl-3,4-dihydro-2-naphthyl)piperidine and the solution was heated for 5 hours at 80°C. After the reaction was over, the solvent was distilled away from the reaction product liquid under a reduced pressure and after adding 5 ml of water to the residue, the product was extracted with chloroform. The extract was washed with 2% aqueous acetic acid solution and then 2% aqueous sodium bicarbonate solution and after drying over anhydrous magnesium sulfate, the solvent was distilled away from the extract. Then, 10 ml of ether was added to the residue, the powder precipitated was recovered by filtration, and reprecipitated from chloroform-ether to provide 0.6g of N-(6-ethyl-3,4-dihydro-2-naphthyl)-tetracycline having a melting point of 172° – 176°C.

Elemental analysis as $C_{34}H_{38}N_2O_8$:

|  | C (%) | H (%) | N (%) |
|---|---|---|---|
| Calculated: | 67.99 | 6.04 | 4.66 |
| Found: | 67.86 | 5.87 | 4.78 |

EXAMPLE 20

In 38 ml of dimethylformamide was dissolved 3.80g of tetracycline hydrochloride and after adding to the solution 3.17g of N-(2-indenyl)piperidine, the mixture was stirred for 16 hours at 50° – 60°C. After the reaction was over, the reaction product liquid was concentrated under a reduced pressure, dissolved in chloroform, and washed thrice with water. Insoluble matters precipitated were filtered off. The chloroform layer was then concentrated under a reduced pressure and ether-n-hexane (1 : 10 in volume ratio) solvent mixture was added to the concentrate, whereby a precipitate was formed. The precipitate was recovered by filtration, dissolved in a small amount of chloroform, and ether was added to the solution, whereby a precipitate was formed. The precipitate was recovered by filtration, dissolved in chloroform, and the solution was washed with 2% aqueous acetic acid solution and then water. After drying the solution over anhydrous magnesium sulfate, the solution was concentrated under a reduced pressure and an ether-n-hexane (1 : 10 in volume ratio) solvent mixture was added to the concentrate to form a precipitate, which was recovered by filtration to provide 0.3g of N-(2-indenyl)tetracycline.

Elemental analysis as $C_{31}H_{30}N_2O_8$:

|  | C (%) | H (%) | N (%) |
|---|---|---|---|
| Calculated: | 66.65 | 5.41 | 5.02 |
| Found: | 66.38 | 5.66 | 5.16 |

EXAMPLE 21

In 7 ml of dimethylformamide was dissolved 0.8g of 5-oxytetracycline and after adding to the solution 0.9g of 3-methyl-2-piperidino-3-p-tolyl-1-butene and further 0.27 ml of 6.5 N aqueous hydrogen choloride in dimethylformamide, the mixture was stirred for 4 hours at room temperature. After the reaction was over, the reaction product liquid was concentrated under a reduced pressure and after adding 10 ml of water, the product was extracted twice each with 30 ml of chloroform. The extract was washed with water, 2% acetic acid solution, and then water and after drying over anhydrous magnesium sulfate, the solvent was distilled away from the extract under a reduced pressure. Then, ether and petroleum ether were added to the residue and the crystalline powder thus formed was recovered by filtration. The product was reprecipitated from chloroform to provide 0.4g of N-[1-(1-methyl-1-ptolylethyl)ethenyl] -5-oxytetracycline.

Elemental analysis as $C_{34}H_{38}N_2O_9$:

|  | C (%) | H (%) | N (%) |
|---|---|---|---|
| Calculated: | 66.01 | 6.19 | 4.53 |
| Found: | 65.89 | 6.35 | 4.70 |

EXAMPLE 22

In 13 ml of dimethylformamide was dissolved 1.3g of 6-dimethyl-7-chlorotetracycline hydrochloride and after adding to the solution 1.26g of 3-methyl-2-piperidino-3-p-tolyl-1-butene, the mixture was stirred for 6 hours at room temperature. Thereafter, by following the same procedure as in Example 16, 0.8g of N-[1-(1-methyl-1-p-tolylethyl)ethenyl]-6-dimethyl-7-chlorotetracycline was obtained.

Elemental analysis as $C_{33}H_{35}N_2O_8Cl$:

|  | C (%) | H (%) | N (%) | Cl (%) |
|---|---|---|---|---|
| Calculated: | 63.61 | 5.66 | 4.50 | 5.69 |
| Found: | 63.30 | 5.74 | 4.57 | 5.60 |

EXAMPLE 23

In 3 ml of dimethylformamide was dissolved 1.2g of 7-chlorotetracycline hydrochloride and after adding to the solution 1.14g of 3-methyl-2-piperidino-3-p-tolyl-1-butene, the mixture was stirred for 6 hours at room temperature. Thereafter, by following the same procedure as in Example 16, 0.5g of N-[1-(1-methyl-1-p-tolylethyl)ethenyl]-7-chlorotetracycline was obtained.

Elemental analysis as $C_{34}H_{37}N_2O_8Cl$:

|  | C (%) | H (%) | N (%) | Cl (%) |
|---|---|---|---|---|
| Calculated: | 64.10 | 5.86 | 4.40 | 5.56 |
| Found: | 63.94 | 5.79 | 4.54 | 5.52 |

EXAMPLE 24

In 16 ml of dimethylformamide was dissolved 1.65g of 5-oxy-6-deoxy-tetracycline hydrochloride and after adding to the solution 1.65g of 3-methyl-2-piperidino-3-p-tolyl-1-butene, the mixture was stirred for 5 hours at room temperature. Thereafter, by following the same procedure as in Example 16, 0.5g of N-[1-(1-methyl-1-p-tolylethyl)ethenyl]-5-oxy-6-deoxytetracycline was obtained.

Elemental analysis as $C_{34}H_{38}N_2O_8$:

|  | C (%) | H (%) | N (%) |
|---|---|---|---|
| Calculated: | 67.76 | 6.36 | 4.65 |
| Found: | 67.50 | 6.34 | 4.57 |

EXAMPLE 25

In 5 ml of dimethylformamide was dissolved 430 mg of tetracycline hydrochloride and after adding to the solution 560 mg of 1-p-methylsulfonylphenyl-2-morpholino-1-propene, the mixture was stirred for 24 hours at room temperature. Thereafter, by following the same procedure as in Example 21, 120 mg of N-(1-methyl-2-p-methylsulfonyl-phenylethenyl)tetracycline was obtained.

Elemental analysis as $C_{32}H_{34}N_2O_{10}S$:

|  | C (%) | H (%) | N (%) |
|---|---|---|---|
| Calculated: | 60.18 | 5.37 | 4.39 |
| Found: | 59.80 | 5.32 | 4.04 |

EXAMPLE 26

In 5 ml of dimethylformamide was dissolved 477 mg of tetracycline hydrochloride and then after adding 338 mg of N-(4,5-dihydro-3-thienyl)piperidine to the solution, the mixture was stirred for 7 hours at room temperature. After the reaction was over, the solvent was distilled away from the reaction product liquid under a reduced pressure, water was added to the residue thus obtained, and the crystal formed was recovered by filtration to provide 353 mg of N-(dihydro-3-thienyl)-tetracycline.

In addition, the filtrate was extracted with chloroform and the extract was washed with water, dried over anhydrous sodium sulfate, the solvent was distilled away under a reduced pressure, the residue thus obtained was dissolved in acetone, and ether was added to the solution to form a precipitate, which was recovered by filtration to provide 23 mg of N-(4,5-dihydro-3-thienyl)tetracycline.

| Elemental analysis as $C_{28}H_{28}O_8N_2S$: | | | |
|---|---|---|---|
| | C (%) | H (%) | N (%) | S (%) |
| Calculated: | 59.08 | 5.34 | 5.30 | 6.07 |
| Found: | 60.03 | 5.00 | 5.33 | 5.86 |

EXAMPLE 27

In 20 ml of dimethylformamide was dissolved 2.0g of 6-demethyl-7-chlorotetracycline hydrochloride and after adding to the solution 1.83g of a mixture of 2-piperidino-3-p-tolyl-1-butene and 2-piperidino-3-p-tolyl-2-butene, the mixture was stirred for 6 hours at room temperature.

Thereafter, by following the same procedure as in Example 26, 1.0g of the light yellow powder of N-[1-(1-p-tolylethyl)ethenyl]-6-demethyl-7-chlorotetracycline was obtained.

| Elemental analysis as $C_{32}H_{33}N_2O_6Cl$: | | | |
|---|---|---|---|
| | C (%) | H (%) | N (%) | Cl (%) |
| Calculated: | 63.10 | 5.46 | 4.60 | 5.82 |
| Found: | 62.81 | 5.33 | 4.78 | 6.01 |

EXAMPLE 28

In 12 ml of dimethylformamide was dissolved 1.5g of tetracycline hydrochloride and after adding to the solution 2.0g of 2-morpholino-3-(2-thienyl)-2-pentene, the mixture was stirred for 6 hours at room temperature.

After the reaction was over, the solvent was distilled away from the reaction product liquid under a reduced pressure and after adding water and chloroform to the residue followed by sufficient shaking, the chloroform layer formed was recovered. The extract was washed with 2% aqueous acetic acid solution and then water and after drying over anhydrous magnesium sulfate, the solvent was distilled away under a reduced pressure. When ether and petroleum ether were added to the residue, a precipitate was formed, which was recovered by filtration and dissolved in chloroform. When ether and petroleum ether were added to the solution and the product was reprecipitated, 1.0g of the light yellow powder of N-[1-methyl-2-(2-thienyl)-1-butenyl]tetracycline was obtained.

| Elemental analysis as $C_{31}H_{34}N_2O_8S$: | | | |
|---|---|---|---|
| | C (%) | H (%) | N (%) | S (%) |
| Calculated: | 62.61 | 5.76 | 4.71 | 5.39 |
| Found: | 62.75 | 5.82 | 4.96 | 5.52 |

EXAMPLE 29

In 40 ml of dimethylformamide was dissolved 5.5g of tetracycline hydrochloride and after adding to the solution 6.0g of 3-methyl-2-morpholino-3-(2-thienyl)-1-butene, the mixture was stirred for 7 hours at room temperature. Thereafter, by following the same procedure as in Example 28, 4.0g of the light yellow powder of N-[1-methyl-1-(2-thienyl)-ethyl)-ethenyl]tetracycline was obtained.

| Elemental analysis as $C_{31}H_{34}N_2O_8S$: | | | |
|---|---|---|---|
| | C (%) | H (%) | N (%) | S (%) |
| Calculated | 62.61 | 5.76 | 4.71 | 5.39 |
| Found: | 62.69 | 5.98 | 4.51 | 5.48 |

EXAMPLE 30

In 2.5 ml of dimethylformamide was dissolved 255 mg of tetracycline hydrochloride and after adding to the solution 350 mg of crude 1-cyclohexyl-2-morpholino-1-propene, the mixture was stirred for 5 hours at room temperature. After the reaction was over, the reaction product liquid was concentrated under a reduced pressure and after adding a small amount of water to the concentrate, the product was extracted with chloroform. The extract was washed with water, twice with 2% aqueous acetic acid solution, and then thrice with water and after drying over anhydrous magnesium sulfate, the extract was concentrated under a reduced pressure to such an extent that a small amount of chloroform remained. When ether and petroleum ether was added to the concentrate, a precipitate was formed. The precipitate was recovered by filtration, dissolved in a small amount of chloroform, and after adding ether and petroleum ether, the product was reprecipitated, whereby 40 mg of the yellow powder of N-(2-cyclohexyl-1-methylethenyl)tetracycline was obtained.

| Elemental analysis as $C_{31}H_{38}N_2O_8$: | | |
|---|---|---|
| | C (%) | H (%) | N (%) |
| Calculated: | 65.71 | 6.76 | 4.94 |
| Found: | 65.50 | 6.92 | 5.11 |

EXAMPLE 31

In 16 ml of dimethylformamide was dissolved 1.67g of tetracycline hydrochloride and after adding to the solution 1.63 g of mixture of 3-methyl-2-piperidinoindene and 1-methyl-2-piperidinoindene, the mixture was stirred for 17 hours at 40° – 50°C.

Thereafter, by following the same procedure as in Example 30, 120 mg of the yellow powder of N-(3-methyl-2-indenyl)tetracycline was obtained.

| Elemental analysis as $C_{32}H_{32}N_2O_8$: | | |
|---|---|---|
| | C (%) | H (%) | N (%) |
| Calculated: | 67.12 | 5.63 | 4.89 |
| Found: | 66.90 | 5.88 | 5.20 |

EXAMPLE 32

To 7 ml of dimethylformamide were added 1g of 1,2-dipiperidino-1-propene and 1g of tetracycline hydrochloride under ice-cooling and the mixture was stirred for 2 hours in an ice-water bath. After the reaction was over, the solvent was distilled away from the reaction product liquid under a reduced pressure and after adding 10 ml of water to the residue, the product was extracted thrice each with 5 ml of chloroform. The chloroform extract was then extracted with 2% aqueous acetic acid solution until the aqueous layer became acidic. To the extract was added sodium bicarbonate to adjust the pH thereof to about 7.5 and after washing the extract with 10 ml of ether, the product was extracted thrice each with 10 ml of chloroform. When the chloroform was distilled away from the chloroform extract under a reduced pressure and n-hexane was added to the residue, a powder was precipitated. The powder was recovered by filtration to provide 0.7g of N-(1-methyl-2-piperidinoethenyl)tetracycline.

Elemental analysis as $C_{30}H_{37}N_3O_8$:

|  | C (%) | H (%) | N (%) |
|---|---|---|---|
| Calculated: | 63.48 | 6.57 | 7.40 |
| Found: | 63.26 | 6.63 | 7.23 |

EXAMPLE 33

In 10 ml of dimethylformamide was dissolved 1.05g of tetracycline hydrochloride and after adding to the solution 1.2g of 1-(2-quinolyl)-2-piperidino-1-propene, the mixture was stirred for 5 hours at room temperature. After the reaction was over, the reaction product liquid was concentrated under a reduced pressure and after adding water to the concentrate, the product was extracted with chloroform. The extract was washed with water, 2% aqueous acetic acid solution, and then water and after drying over anhydrous sodium sulfate, chloroform was distilled away. When ether and petroleum ether were added to the residue, a precipitate was formed. The precipitate was recovered by filtration and dissolved in a small amount of chloroform. Then, ether and petroleum ether were added followed by reprecipitation to provide 0.2g of N-[1-methyl-2-(2-quinolyl)ethenyl]tetracycline.

Elemental analysis as $C_{34}H_{33}N_3O_8$:

|  | C (%) | H (%) | N (%) |
|---|---|---|---|
| Calculated: | 66.77 | 5.44 | 6.87 |
| Found: | 66.33 | 5.64 | 7.00 |

EXAMPLE 34

In 13 ml of dimethylformamide was dissolved 1.904g of tetracycline hydrochloride and after adding 1.224g of 3-piperidino-2-pentene to the solution, the mixture was stirred for 3 hours at room temperature. After the reaction was over, piperidine hydrochloride precipitated in the reaction was filtered off and the solvent was distilled away from the filtrate. When 3 ml of water was added to the residue, 1.3g of crystalline N-(1-ethyl-1-propenyl)tetracycline was obtained.

Elemental analysis as $C_{27}H_{32}N_2O_8$:

|  | C (%) | H (%) | N (%) |
|---|---|---|---|
| Calculated: | 63.27 | 6.29 | 5.47 |
| Found: | 63.36 | 6.51 | 6.00 |

EXAMPLES 35 – 38

By the same way as above, the following compounds shown by the formula were prepared.

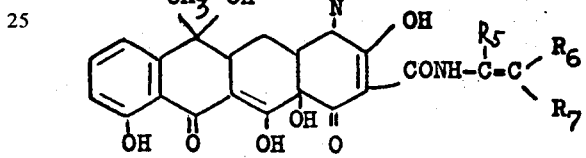

| Number of Example | $R_5$ | $R_6$ | $R_7$ | Calculated C(%) | H(%) | N(%) | Found C(%) | H(%) | N(%) |
|---|---|---|---|---|---|---|---|---|---|
| 35 | —CH$_3$ | —H | —C$_6$H$_4$-Cl | 58.55 | 4.59 | 4.55 | 58.32 | 4.37 | 4.81 |
| 36 | —CH$_3$ | —H | —C$_6$H$_3$Cl-Cl | 57.50 | 4.98 | 4.33 | 57.68 | 5.09 | 4.55 |
| 37 | —CH$_3$ | —H | —C$_6$H$_4$-N(CH$_3$)$_2$ | 65.66 | 6.18 | 6.96 | 65.30 | 6.32 | 6.73 |
| 38 | —CH$_2$CH$_2$—S—CH$_2$— | | —H | 59.77 | 5.16 | 5.16 | 59.44 | 6.09 | 5.46 |

EXAMPLE 39

In 10 ml of dimethylformamide was dissolved 1.0g of tetracycline hydrochloride and after adding to the solution 0.7g of N-cyclohexenylpiperidine, the mixture was stirred for 5 hours at room temperature. After the reaction was over, the solvent was distilled away from the reaction product liquid under a reduced pressure and when water was added to the residue obtained and then the pH of the solution was adjusted to 5 with 1 N hydrochloric acid, a precipitate was formed. The precipitate was recovered by filtration, dissolved in chloroform after being washed with water, and reprecipitated from chloroformether to provide 0.6g of N-cyclohexenyltetracycline.

Nuclear magnetic resonance: Alkene hydrogen

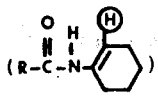

τ 4.0 (1H) (CD Cl₃)
Elemental analysis as $C_{28}H_{32}N_2O_8 \cdot H_2O$:

|  | C (%) | H (%) | N (%) |
|---|---|---|---|
| Calculated: | 61.98 | 6.32 | 5.16 |
| Found: | 61.58 | 6.13 | 5.19 |

EXAMPLE 40

In 10 ml of dimethylformamide was dissolved 1.0g of tetracycline hydrochloride and after adding to the solution 0.75g of N-cycloheptenylpiperidine, the mixture was stirred for 5 hours at room temperature. Thereafter, by following the same procedure as in Example 39, 0.65g of N-cycloheptenyltetracycline was obtained.

Nuclear magnetic resonance: Alkene hydrogen

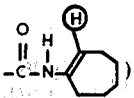

τ 3.8 (1H) (CD Cl₃)
Elemental analysis as $C_{29}H_{34}N_2O_8 \cdot H_2O$:

|  | C (%) | H (%) | N (%) |
|---|---|---|---|
| Calculated: | 62.58 | 6.52 | 5.03 |
| Found: | 62.28 | 6.38 | 5.25 |

EXAMPLE 41

In 10 ml of dimethylformamide was dissolved 1.0g of tetracycline hydrochloride and after adding to the solution 0.8g of N-cyclooctenylpiperidine, the mixture was stirred for 5 hours at room temperature. Thereafter, by following the same procedure as in Example 39, 1.1g of n-cyclooctenyltetracycline was obtained.

Nuclear magnetic resonance: Alkene hydrogen
τ 3.9 (1H) (CD Cl₃)

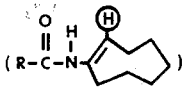

Elemental analysis as $C_{30}H_{36}N_2O_8 \cdot H_2O$:

|  | C (%) | H (%) | N (%) |
|---|---|---|---|
| Calculated: | 63.14 | 6.71 | 4.91 |
| Found: | 63.02 | 6.58 | 4.72 |

EXAMPLE 42

To 5 ml of dimethylformamide were added 558 mg of 2-piperidino-1-m-tolyl-1-butene and 625 mg of tetracycline hydrochloride and then the mixture was stirred for 6 hours at room temperature.

After the reaction was over, the solvent was distilled away from the reaction product liquid under a reduced pressure and the residue obtained was extracted with chloroform. The chloroform extract was washed with 3% aqueous acetic acid solution and then water and after drying over anhydrous magnesium sulfate, the solvent was distilled away under a reduced pressure. The residue obtained was dissolved in a small amount of acetone, petroleum was added to the solution, and the precipitate thus formed was recovered by filtration and dried to provide 730 mg of the light yellow powder of N-[1-ethyl-2-m-tolylethenyl]tetracycline.

Elemental analysis as $C_{33}H_{36}N_2O_8$:

|  | C (%) | H (%) | N (%) |
|---|---|---|---|
| Calculated: | 67.33 | 6.16 | 4.76 |
| Found: | 67.59 | 6.33 | 4.87 |

EXAMPLES 43 – 46

By the same way as above, the following compounds were prepared.

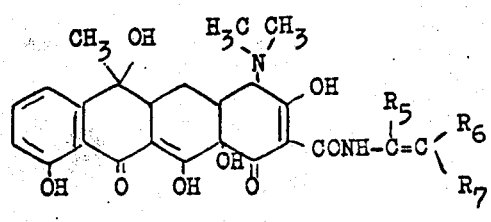

| Number of Example | R₅ | R₆ | R₇ | Calculated C(%) H(%) N(%) | Found C(%) H(%) N(%) |
|---|---|---|---|---|---|
| 43 | —CH₂CH₃ | phenyl-CH₃ | —H | 67.33  6.16  4.76 | 67.61  6.43  4.49 |
| 44 | —CH₂CH₃ | phenyl-CH₃ | —CH₃ | 67.76  6.36  4.65 | 68.18  6.71  4.23 |
| 45 | —CH₂CH₃ | phenyl(CH₃) | —CH₃ | 67.76  6.36  4.65 | 67.28  6.08  4.50 |
| 46 | —CH₃ | —CH₂CH₃ | —H | 63.27  6.29  5.47 | 63.01  6.53  5.18 |

EXAMPLE 47

To 4 ml of dimethylformamide were added 550 mg of 3-methyl-2-piperidino-3-m-tolyl-1-butene and 490 mg of tetracycline hydrochloride and the mixture was stirred for 5 hours at room temperature. After the reaction was over, the solvent was distilled away from the reaction product liquid under a reduced pressure. The residue obtained was dissolved in chloroform and the chloroform solution was washed with 3% aqueous acetic acid solution and then water and after drying over anhydrous magnesium sulfate, the solvent was distilled away. The residue was dissolved in ether, and after adding petroleum ether to the solution, the precipitate formed was recovered by filtration and dried to provide 453 mg of N-[1-(1-methyl-1-m-tolylethyl)ethenyl]tetracycline.

| Elemental analysis as $C_{34}H_{38}N_2O_8$: | C (%) | H (%) | N (%) |
|---|---|---|---|
| Calculated: | 67.76 | 6.36 | 4.65 |
| Found: | 67.39 | 6.50 | 4.97 |

EXAMPLES 48 – 52

By the same way as above, the following examples were prepared.

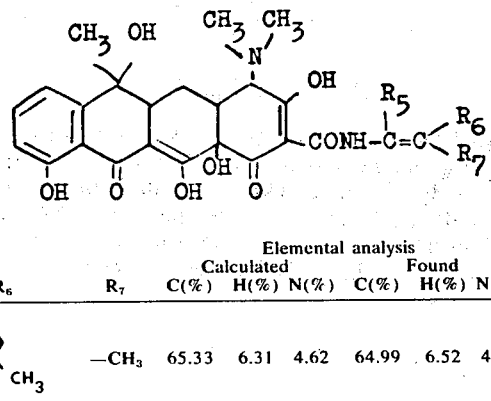

| Number of Example | R₅ | R₆ | R₇ | Calculated C(%) H(%) N(%) | Found C(%) H(%) N(%) |
|---|---|---|---|---|---|
| 48 | —CH₃ | phenyl-CH₃ | —CH₃ | 65.33  6.31  4.62 | 64.99  6.52  4.77 |
| 49 | —C(CH₃)(CH₂CH₃)-phenyl-CH₃ | —H | —H | 66.23  6.67  4.41 | 66.02  6.51  4.09 |
| 50 | —C(H)(CH₃)-phenyl-CH₃ | —CH₃ | —H | 67.76  6.36  4.65 | 67.55  6.21  4.87 |
| 51 | —CH₃ | phenyl-CH₃ | —CH₃ | 67.33  6.16  4.76 | 67.83  6.01  4.77 |
| 52 | phenyl-CH₂CH₂— |  | —H | 66.43  6.62  4.84 | 66.33  6.54  4.79 |

EXAMPLE 53

In 40 ml of dimethylformamide was dissolved 4.1g of tetracycline hydrochloride and after adding dropwise 4g of 1-(p-chlorophenyl)-2-piperidinopropene to the solution at room temperature, the mixture was stirred for 5 hours at room temperature. After the reaction was over, the solvent was distilled away from the reaction product liquid under a reduced pressure and the residue was washed with water and dissolved in 200 ml of chloroform. Further, the solution was washed thrice with water and after drying over anhydrous sodium sulfate, chloroform was distilled away. When ether was added to the residue, a solid product was precipitated, which was recovered by filtration, dissolved in 200 ml of chloroform, and washed twice with 2% aqueous acetic acid solution. The solution was further washed thrice with water and after drying over anhydrous sodium sulfate, chloroform was distilled away.

When ether-petroleum ether (1 : 3) mixture was added to the residue, 3g of N-(2-p-chlorophenyl-1-methylethenyl)tetracycline was precipitated.

Elemental analysis as $C_{31}H_{31}N_2O_8Cl$:

| | C (%) | H (%) | N (%) | Cl (%) |
|---|---|---|---|---|
| Calculated: | 62.57 | 5.25 | 4.71 | 5.96 |
| Found: | 62.40 | 5.45 | 4.80 | 6.01 |

EXAMPLES 54 – 64

By the same way as above, the following compounds were prepared.

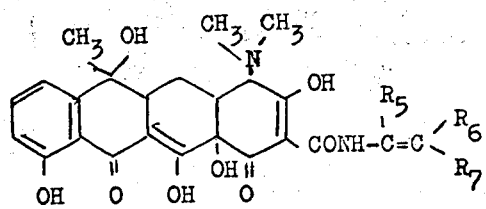

| Number of Example | $R_5$ | $R_6$ | $R_7$ | Calculated C(%) | H(%) | N(%) | Found C(%) | H(%) | N(%) |
|---|---|---|---|---|---|---|---|---|---|
| 54 | —CH$_3$ | —CH$_3$ | —C$_6$H$_5$ | 66.89 | 5.96 | 4.87 | 67.01 | 6.25 | 4.65 |
| 55 | —CH$_3$ | —H | -C$_6$H$_3$(OCH$_3$)$_2$ | 63.86 | 5.85 | 4.51 | 63.51 | 6.12 | 4.35 |
| 56 | —CH$_3$ | —H | -C$_6$H$_4$CH$_2$CH$_3$ | 67.33 | 6.16 | 4.76 | 67.13 | 6.21 | 4.83 |
| 57 | —CH$_3$ | —H | -C$_6$H$_3$(CH$_3$)$_2$ | 67.33 | 6.16 | 4.76 | 67.10 | 6.17 | 4.86 |
| 58 | —CH$_3$ | —H | —CH$_3$ | 63.86 | 6.51 | 5.32 | 63.58 | 6.46 | 5.41 |
| 59 | —CH$_2$CH$_2$CH$_2$CH$_2$— | | —CH$_3$ | 64.67 | 6.36 | 5.20 | 64.26 | 6.15 | 5.55 |
| 60 | -CH$_2$CH$_2$CHCH$_2$- (with phenyl) | | —H | 66.01 | 6.19 | 4.53 | 65.99 | 6.13 | 4.24 |
| 61 | (phenyl)CH$_2$CH$_2$- | | —H | 67.12 | 5.63 | 4.89 | 66.70 | 5.69 | 5.03 |
| 62 | —H | —O—CH=CHCH$_2$CH$_2$— | —CONH-C$_6$H$_5$ | 62.45 | 5.61 | 5.20 | 62.60 | 5.90 | 5.10 |
| 63 | —CH$_2$CH$_2$CH$_2$CH$_2$— | | | 65.31 | 5.79 | 6.52 | 65.18 | 5.62 | 6.33 |
| 64 | —CH$_3$ | —C$_6$H$_5$ | —SCH$_3$ | 63.35 | 5.65 | 4.62 | 62.87 | 5.91 | 4.41 |

EXAMPLE 65

In 10 ml of dimethylformamide was dissolved 1.0g of tetracycline hydrochloride and after adding 1.15g of 1,1-diphenyl-2-piperidinopropene to the solution, the mixture was stirred for 7 hours at room temperature. After the reaction was over, the solvent was distilled away from the reaction product liquid under a reduced pressure and after adding water to the residue, the product was extracted with chloroform. After washing the chloroform layer a few times with water, chloroform was distilled away, an ether-petroleum ether mixture was added to the residue, the precipitate thus formed was recovered by filtration. The precipitate was dissolved in chloroform and after washing the solution with 2% aqueous acetic acid solution and then water, chloroform was distilled away. When petroleum ether was added to the residue and the precipitate thus formed was recovered and purified from an ether-petroleum ether mixture, 450 mg of N-(1-methyl-2,2-diphenylethenyl)tetracycline was obtained.

Elemental analysis as $C_{37}H_{36}N_2O_8$:

| | C (%) | H (%) | N (%) |
|---|---|---|---|
| Calculated: | 69.80 | 5.70 | 4.40 |

-continued

Elemental analysis as $C_{37}H_{36}N_2O_8$:

| | C (%) | H (%) | N (%) |
|---|---|---|---|
| Found: | 69.91 | 5.74 | 4.42 |

EXAMPLES 66 – 95

By the same way as above, the following compounds were prepared.

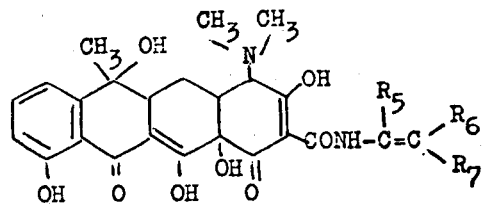

| Number of Example | $R_5$ | $R_6$ | $R_7$ | Elemental analysis Calculated C(%) | H(%) | N(%) | Found C(%) | H(%) | N(%) |
|---|---|---|---|---|---|---|---|---|---|
| 66 | —H | —$CH_3$ | —phenyl | 66.42 | 5.75 | 5.00 | 66.63 | 5.90 | 4.85 |
| 67 | —$CH_3$ | —H | —pyridyl | 64.16 | 5.56 | 7.48 | 63.98 | 5.77 | 7.48 |
| 68 | —$CH_3$ | —H | —(2-methylphenyl) | 65.08 | 5.80 | 4.74 | 64.96 | 5.89 | 4.81 |
| 69 | —$CH_3$ | —H | —$C_6H_4$-$CH_3$ | 66.89 | 5.96 | 4.87 | 66.72 | 5.97 | 5.20 |
| 70 | —$CH_3$ | —H | —$C_6H_4$-F | 64.35 | 5.40 | 4.84 | 64.12 | 5.47 | 5.00 |
| 71 | —$CH_3$ | —H | —$C_6H_4$-$CH(CH_3)_2$ | 67.76 | 6.36 | 4.65 | 67.48 | 6.32 | 4.65 |
| 72 | —$CH_3$ | —H | —(3-methylphenyl) | 66.89 | 5.96 | 4.87 | 66.63 | 6.14 | 5.05 |
| 73 | —$CH_3$ | —H | —(2-methylphenyl) | 66.89 | 5.96 | 4.87 | 66.78 | 6.09 | 4.91 |
| 74 | —CH(CH_3)_2 | —$CH_3$ | —$CH_3$ | 64.43 | 6.71 | 5.18 | 64.21 | 6.63 | 5.32 |
| 75 | —$CH_3$ | —H | —$C_6H_4$-$CH_2CH_2CH_3$ | 67.76 | 6.36 | 4.65 | 67.74 | 6.46 | 4.71 |
| 76 | —$CH_3$ | —H | —$C_6H_4$-$(CH_2)_3CH_3$ | 68.17 | 6.54 | 4.54 | 67.91 | 6.55 | 4.58 |
| 77 | —phenyl | —H | —$CH_3$ | 66.42 | 5.75 | 5.00 | 66.19 | 5.75 | 4.92 |
| 78 | —$CH_3$ | —$C_6H_4$-$CH_3$ | —$CH_2CH_3$ | 67.76 | 6.36 | 4.65 | 67.52 | 6.26 | 4.68 |
| 79 | —C(CH)(SCH_3)(phenyl) | —H | —H | 63.86 | 5.85 | 4.51 | 63.66 | 5.90 | 4.56 |
| 80 | —C(CH_3)_2(furyl) | —H | —H | 64.35 | 5.92 | 4.84 | 64.17 | 6.02 | 5.00 |

-continued

| Number of Example | $R_5$ | $R_6$ | $R_7$ | Calculated C(%) | H(%) | N(%) | Found C(%) | H(%) | N(%) |
|---|---|---|---|---|---|---|---|---|---|
| 81 |  | —H | —H | 66.55 | 5.74 | 6.85 | 66.24 | 5.63 | 6.69 |
| 82 |  | —H | —H | 68.17 | 6.54 | 4.54 | 67.92 | 6.51 | 4.65 |
| 83 | —CH$_3$ | —CH$_2$CH$_2$CH$_3$ |  | 68.17 | 6.54 | 4.54 | 67.96 | 6.54 | 4.83 |
| 84 | —CH$_2$CH$_2$CH$_2$CH$_2$— | |  | 68.39 | 6.23 | 4.56 | 68.11 | 6.30 | 4.26 |
| 85 | —CH$_2$CH$_2$CH$_2$CH$_2$CH$_2$— | |  | 68.77 | 6.41 | 4.46 | 68.48 | 6.37 | 4.72 |
| 86 | —CH$_2$CH$_3$ | —CH$_2$CH$_3$ |  | 63.15 | 5.96 | 4.61 | 63.01 | 5.75 | 4.82 |
| 87 | —CH$_2$CH$_3$ | —CH$_3$ |  | 62.61 | 5.76 | 4.71 | 62.35 | 5.85 | 4.95 |
| 88 | —CH$_3$ | —CH$_2$CH$_2$CH$_3$ |  | 63.15 | 5.96 | 4.61 | 63.00 | 5.69 | 4.66 |
| 89 | —CH$_3$ | —(CH$_2$)$_3$CH$_3$ |  | 63.65 | 6.15 | 4.50 | 63.85 | 6.41 | 4.30 |
| 90 |  | —H | —H | 63.15 | 5.96 | 4.61 | 62.94 | 5.76 | 4.81 |
| 91 |  | —H | —H | 63.65 | 6.15 | 4.50 | 63.38 | 6.00 | 4.70 |
| 92 |  | —H | —H | 64.85 | 6.12 | 4.73 | 64.95 | 6.22 | 4.60 |
| 93 |  | —H | —H | 65.33 | 6.31 | 4.62 | 65.10 | 6.40 | 4.71 |
| 94 |  | —H | —H | 65.79 | 6.50 | 4.51 | 65.90 | 6.35 | 4.75 |
| 95 | —CH$_3$ | —CH$_2$CH$_3$ |  | 66.65 | 6.07 | 4.44 | 66.38 | 6.27 | 4.64 |

EXAMPLE 96

In 17 ml of dimethylformamide was dissolved 1.7g of tetracycline hydrochloride and after adding dropwise 1.3g of 4-piperidino-3-heptene to the solution at room temperature, the mixture was stirred for 5 hours at room temperature. After the reaction was over, the solvent was distilled away from the reaction product liquid under a reduced pressure and water was added to the residue, whereby a solid product was precipitated. The precipitate was recovered by filtration to provide 1.8g of N-(1-propyl-1-butenyl)tetracycline. The product was almost pure but the product was dissolved in chloroform, the solution was washed with water, and after drying over anhydrous sodium sulfate, chloroform was distilled away. The residue was dissolved in ether and reprecipitated from n-hexane.

Elemental analysis as C$_{29}$H$_{36}$N$_2$O$_8$:

| | C (%) | H (%) | N (%) |
|---|---|---|---|
| Calculated: | 64.43 | 6.71 | 5.18 |
| Found: | 64.14 | 7.00 | 5.60 |

EXAMPLES 97 – 145

By the same way as above, the following compounds were prepared.

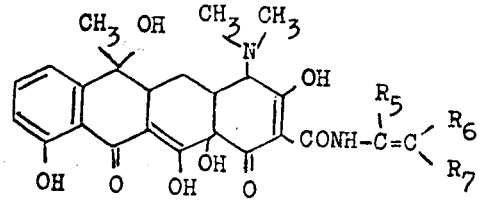

| Number of Ex. | $R_5$ | $R_6$ | $R_7$ | Calculated C(%) | H(%) | N(%) | Found C(%) | H(%) | N(%) |
|---|---|---|---|---|---|---|---|---|---|
| 97 | —H | —CH₂CH₃ | —CH₂CH₃ | 61.75 | 6.66 | 5.14 | 61.32 | 6.81 | 5.60 |
| 98 | —CH₃ | —H | —C₆H₅ | 66.42 | 5.75 | 5.00 | 65.96 | 5.99 | 5.26 |
| 99 | —C₆H₄Cl | —H | —H | 62.02 | 5.03 | 4.82 | 61.74 | 5.20 | 5.12 |
| 100 | —H | —H | —CH₃ | 59.75 | 6.02 | 5.57 | 59.63 | 6.36 | 5.41 |
| 101 | —H | —CH₃ | —CH₃ | 62.64 | 6.07 | 5.62 | 62.52 | 6.19 | 5.81 |
| 102 | —C₆H₅ | —H | —C₆H₅ | 69.44 | 5.50 | 4.50 | 69.24 | 5.73 | 4.85 |
| 103 | —CH₂—C₆H₅ | —H | —C₆H₅ | 69.80 | 5.70 | 4.40 | 69.64 | 5.86 | 4.79 |
| 104 | —CH₃ | —H | —C₆H₄Cl | 62.57 | 5.25 | 4.71 | 62.51 | 5.35 | 4.91 |
| 105 | —CH₃ | —CH₃ | —C₆H₄Cl | 63.10 | 5.46 | 4.60 | 62.95 | 5.29 | 4.85 |
| 106 | —CH₃ | —CH₂CH=CH₂ | —C₆H₄Cl | 64.30 | 5.55 | 4.41 | 64.11 | 5.64 | 4.75 |
| 107 | —CH₃ | —H | —C₆H₄Br | 58.22 | 4.89 | 4.38 | 58.01 | 4.95 | 4.58 |
| 108 | —C(CH₃)₂—C₆H₄Cl | —H | —H | 63.61 | 5.66 | 4.50 | 63.33 | 5.74 | 4.76 |
| 109 | —CH₃ | —H | —O—C₆H₅ | 64.58 | 5.59 | 4.86 | 64.48 | 5.81 | 5.05 |
| 110 | —CH₃ | —H | —C₆H₄OCH₃ | 65.07 | 5.80 | 4.74 | 65.30 | 6.10 | 5.00 |
| 111 |  | —CH₂CH₂—N(CH₃)—CH₂— | —H | 60.31 | 6.33 | 7.54 | 59.88 | 6.33 | 8.01 |
| 112 | —CH₃ | —(CH₂)₄CH₃ | —H | 64.97 | 6.91 | 5.05 | 64.81 | 7.66 | 5.13 |
| 113 | —CH₃ | —C₄H₃S (thienyl) | —H | 61.47 | 5.34 | 4.94 | 61.56 | 5.05 | 5.04 |
| 114 | —C(CH₃)₂—C₆H₅ | —H | —H | 67.33 | 6.16 | 4.76 | 67.13 | 6.16 | 5.01 |
| 115 | —C(CH₃)₂—C₆H₄—CH₂CH₃ | —H | —H | 68.17 | 6.54 | 4.54 | 68.45 | 6.68 | 4.75 |
| 116 | —CH₃ | —C₆H₄—CH₂CH₃ | —CH₃ | 67.76 | 6.36 | 4.65 | 67.77 | 6.39 | 4.77 |
| 117 | —C(CH₃)(CH₂CH₃)—C₆H₄—CH₃ | | —H | 68.17 | 6.54 | 4.54 | 68.21 | 6.73 | 4.71 |
| 118 | —CH₃ | —CH₂—C₆H₅ | —H | 66.89 | 5.97 | 4.87 | 66.85 | 6.19 | 5.18 |
| 119 | —CH₃ | —C₆H₄—OCH₃ | —CH₃ | 65.55 | 6.00 | 4.63 | 65.30 | 5.98 | 4.60 |

| Number of Ex. | R₅ | R₆ | R₇ | Elemental analysis Calculated C(%) H(%) N(%) | Found C(%) H(%) N(%) |
|---|---|---|---|---|---|
| 120 | 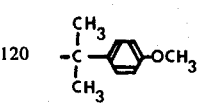 | —H | —H | 66.01 6.19 4.53 | 65.80 6.22 4.78 |
| 121 | —CH₂CH₃ | —6H₃ |  | 67.33 6.16 4.76 | 67.07 6.12 5.02 |
| 122 | 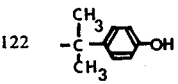 | —H | —H | 65.55 6.00 4.63 | 65.68 5.92 4.82 |
| 123 | —CH₂CH₃ | —CH₃ | 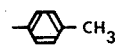 | 67.76 6.36 4.65 | 67.28 6.39 4.28 |
| 124 | —CH₂CH₃ | —CH₂CH₃ | 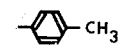 | 68.16 6.54 4.54 | 67.68 6.61 4.71 |
| 125 | —CH₃ | —CH₃ |  | 62.06 5.55 4.82 | 61.83 5.48 4.71 |
| 126 | —CH₃ |  | —H | 62.06 5.55 4.82 | 61.74 5.42 4.51 |
| 127 | —CH₃ |  | —H | 68.84 5.61 4.59 | 68.50 5.56 4.52 |
| 128 | —CH₂CH₂CH₂— | | 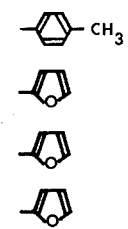 | 67.99 6.04 4.66 | 68.10 6.13 4.73 |
| 129 | —CH₃ | —CH₂CH₃ |  | 64.35 5.92 4.84 | 63.84 5.92 4.94 |
| 130 | —CH₃ | —CH₂CH₂CH₃ |  | 64.85 6.12 4.73 | 64.46 6.08 4.82 |
| 131 | —CH₃ | —CH₃ |  | 65.68 5.88 5.11 | 62.85 5.85 4.65 |
| 132 | —CH₃ | —CH₂CH₃ |  | 69.58 6.00 4.39 | 69.22 6.11 4.22 |
| 133 | —CH₃ | —CH₃ |  | 69.22 5.81 4.48 | 69.13 5.95 4.30 |
| 134 | —CH₃ | —CH₂CH₂CH₃ |  | 69.92 6.18 4.29 | 69.46 6.23 4.39 |
| 135 | 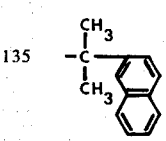 | —H | —H | 69.58 6.00 4.39 | 69.42 6.13 4.33 |
| 136 | —CH₃ | —H |  | 68.84 5.61 4.59 | 69.15 5.71 4.45 |
| 137 | 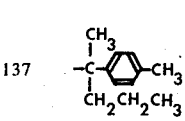 | —H | —H | 68.55 6.71 4.44 | 68.21 6.70 4.46 |
| 138 | —CH₃ | —CH₃ | 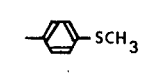 | 63.86 5.85 4.51 | 63.37 5.94 4.43 |

-continued

| Number of Ex. | R₅ | R₆ | R₇ | Calculated C(%) | H(%) | N(%) | Found C(%) | H(%) | N(%) |
|---|---|---|---|---|---|---|---|---|---|
| 139 | —CH₃ | —CH₃ | (5-methyl-2-furyl) | 64.35 | 5.92 | 4.84 | 63.93 | 5.94 | 4.87 |
| 140 | —C(CH₃)₂—(5-methyl-2-furyl) | —H | —H | 64.85 | 6.12 | 4.73 | 64.62 | 6.07 | 4.76 |
| 141 | —CH₃ | —CH₂CH₂CH₃ | (5-methyl-2-furyl) | 65.33 | 6.31 | 4.62 | 64.92 | 6.22 | 4.38 |
| 142 | —CH₃ | —CH(CH₃)₂ | (4-methylphenyl) | 68.17 | 6.54 | 4.54 | 67.94 | 6.59 | 4.61 |
| 143 | —CH₂CH₂CH₂CH₂— | | —CO—(phenyl) | 65.01 | 5.91 | 4.33 | 64.73 | 5.79 | 4.61 |
| 144 | —CH₃ | —H | —COOC₂H₅ | 60.42 | 5.80 | 5.03 | 60.10 | 6.10 | 5.22 |
| 145 | —(CH₂)₄— | —(CH₂)₄— | —SO₂—(4-methylphenyl) | 61.93 | 5.64 | 4.12 | 61.81 | 5.30 | 4.51 |

What is claimed is:

1. An N-alkenyltetracycline derivative represented by the formula

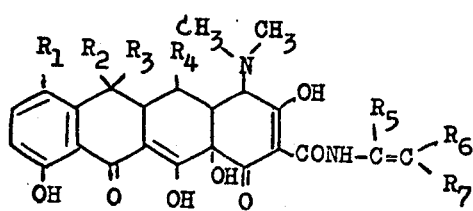

wherein R₁ represents a hydrogen atom or a halogen atom; R₂ represents a hydrogen atom or a methyl group; R₃ represents a hydrogen atom or a hydroxyl group or said R₂ and R₃ when combined with each other, form a methylene group; R₄ represents a hydrogen atom or a hydroxyl group; R₅ represents a hydrogen atom, an alkyl group, a furyl alkyl group or a methyl substituted furyl alkyl group; R₆ represents a hydrogen atom, a furyl group or a methyl substituted furyl group; R₇ represents a hydrogen atom or an alkyl group or said R₆ and R₇ when combined with each other, form a 1-oxa-2-pentenylene group; with the proviso that at least one group of R₅, R₆ and combination group of R₆ and R₇ is a cyclic group including oxygen atom.

2. A compound according to claim 1 which is N-[1-methyl-2-(5-methyl-2-furyl)-1-pentenyl] tetracycline.

3. A compound according to claim 1 in which R₁ and R₄ are hydrogen atoms, R₂ is a methyl group, R₃ is a hydroxyl group, R₅ is a methyl group or a furylalkyl group, R₆ is a hydrogen atom or a methyl-substituted furyl group and R₇ is a hydrogen atom or a lower alkyl group.

4. A compound according to claim 1 which is N-[1-methyl-2-(5-methyl-2-furyl)-1-propenyl] tetracycline.

5. A compound according to claim 1 which is N-{1-[2-(2-furyl)pentyl] ethenyl} tetracycline.

6. A compound according to claim 1 which is N-{1-[2-(2-furyl)hexyl] ethenyl} tetracycline.

7. A compound according to claim 1 which is N-[1-methyl-2-(5-methyl-2-furyl)-1-propenyl] tetracycline.

* * * * *